United States Patent [19]

Randall

[11] 4,245,647
[45] Jan. 20, 1981

[54] ARRHYTHMIA REJECTION CIRCUIT FOR GATED CARDIAC IMAGE DISPLAY SYSTEMS

[75] Inventor: Harvey G. Randall, Oconomowoc, Wis.

[73] Assignee: General Electric Company, Schenectady, N.Y.

[21] Appl. No.: 966,986

[22] Filed: Dec. 6, 1978

[51] Int. Cl.³ .............................................. A61B 00/00
[52] U.S. Cl. ..................................................... 128/659
[58] Field of Search ............... 128/653, 654, 659, 695, 128/696, 702, 703, 705, 706, 708, 709

[56] References Cited

U.S. PATENT DOCUMENTS

| | | | |
|---|---|---|---|
| 3,593,705 | 7/1971 | Thomas et al. | 128/703 |
| 3,618,593 | 11/1971 | Nachev et al. | 128/702 |
| 3,626,932 | 12/1971 | Becker | 128/708 |
| 3,672,353 | 6/1972 | Crovella et al. | 128/702 |
| 3,698,386 | 10/1972 | Fried | 128/705 |
| 3,718,827 | 2/1973 | Ragsdale | 128/702 |
| 3,960,140 | 6/1976 | Buxton | 128/706 |
| 4,033,335 | 7/1977 | Nickles | 128/659 |

Primary Examiner—William E. Kamm

Attorney, Agent, or Firm—Ralph G. Hohenfeldt

[57] ABSTRACT

Signals associated with heart beats occurring at the normal rhythm of the heart and also with extrasystoles or PVCs are fed to a one-shot multivibrator which is enabled to produce clock signals corresponding with incoming heart activity indicating signals such as R-wave signals provided the R-wave signals are spaced in time to correspond with normal heart rhythm. An analog signal corresponding with average heart rate is fed to an integrator. The ramp output of the integrator is fed to one input of a comparator and a reference signal representative of a percentage of time between normal rhythm R-waves is fed to the other input of the comparator. Until the two input signals cross over, the output signal of the comparator is such as to inhibit output of a clock signal from the multivibrator so R-wave signals associated with extrasystoles occurring during the integration or lockout period are not gated through the multivibrator. The clock signals corresponding with predictable rhythmically occurring heart activity signals are used for gating image forming devices and image data devices on and off at identical times in a sequence of heart cycles to produce a stop-motion effect.

5 Claims, 5 Drawing Figures

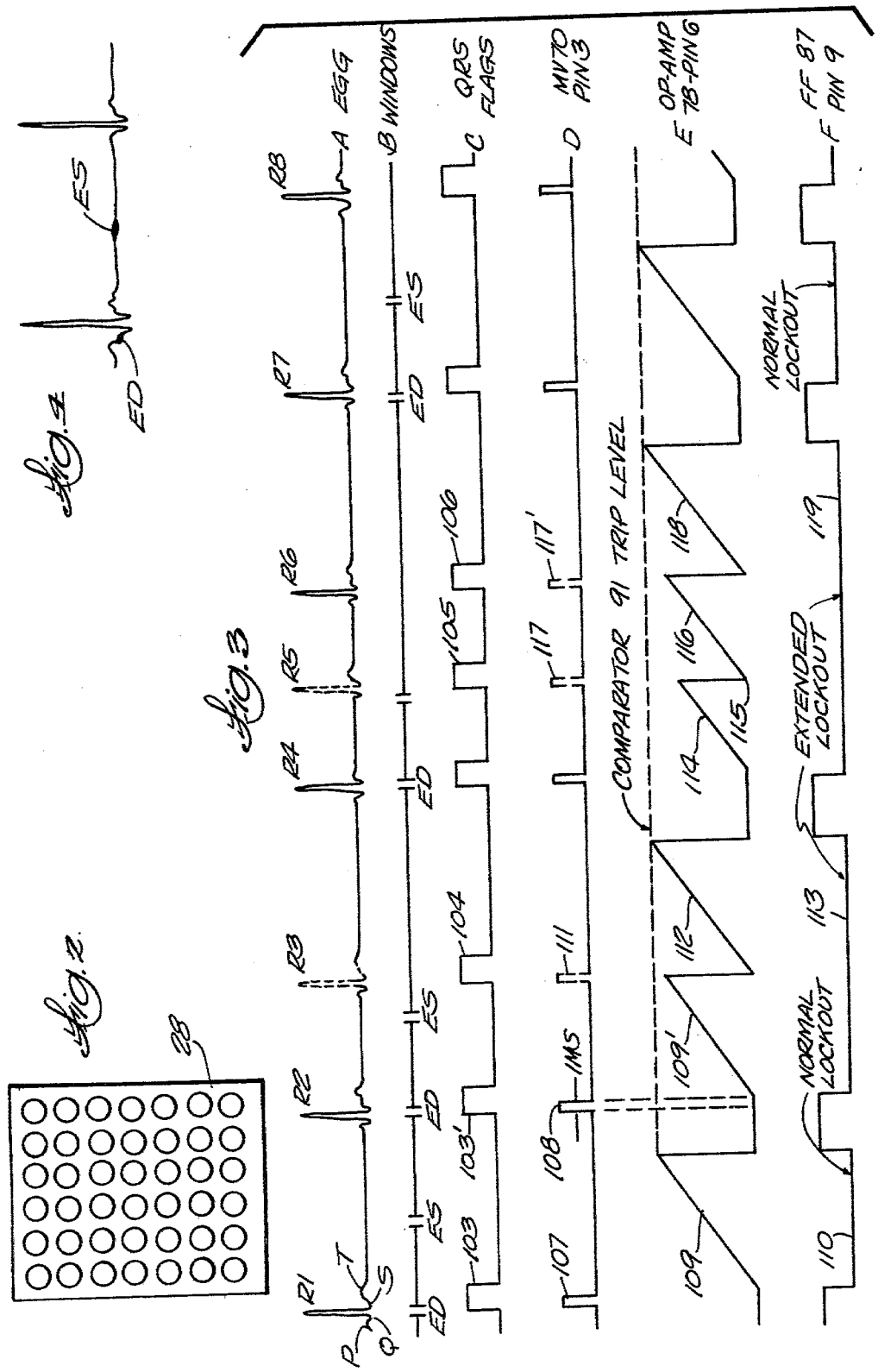

ARRHYTHMIA REJECTION CIRCUIT FOR GATED CARDIAC IMAGE DISPLAY SYSTEMS

This invention is applicable to systems such as conventional and computerized tomography x-ray systems, nuclear radiation systems and ultrasonic radiation camera systems which display images of quiescent organs and moving organs such as the heart.

The invention will be demonstrated and described in reference to a nuclear camera system as used for evaluating cardiac function by taking a nuclear radiation image or exposure of the heart at exactly the same time during successive heart cycles so that an image or sequence of images of sufficient intensity for diagnosis can be integrated. Basically, the invention enables motion of an organ to be stopped. The invention is for permitting data for an image to be gated to the display device only in synchronism with heart beats that occur at the regular or ostensibly normal heart rate and for prohibiting gating upon occurrence of extrasystoles or premature ventricular contractions. If gating of data for each view or image is not initiated at the same time in each heart cycle in relation to some stable reference, such as R-waves occurring at normal sinus rhythm, the stop motion effect will not be obtained and the image or sequence of images will be blurred.

A well-known nuclear camera, hereafter called a gamma camera system, with which the invention may be used is described in U.S. Pat. No. 3,011,057 to Anger. This camera has a large scintillation crystal that is disposed over an organ such as a heart which has been infused with blood containing a radioisotope. The crystal responds to absorption of gamma ray photons emitted from the heart by producing visible light scintillations. A closely packed array of phototubes is located behind the scintillator crystal and their output signals, corresponding with scintillation events, are processed in an analog computer to determine the x and y coordinates of the scintillations and the energies of the gamma photons. The electric pulses which result from the scintillations are fed first to a pulse height analyzer. Pulses falling outside of a narrow energy range, called a window, are rejected and pulses within the window are considered valid. For every pair of valid x and y coordinate signals, a coincident z signal is produced with known electronic circuitry.

The x and y coordinate signals are used to drive the beam deflection control circuits of a cathode ray tube on which the cumulative image of a large number of scintillation events is displayed. The cathode ray tube is unblanked only by z signals so that only valid scintillations are displayed. Typical methods of developing suitable x, y and z signals are described in U.S. Pat. Nos. 3,697,753 and 3,919,556.

Images displayed on the cathode ray tube (CRT) screen are usually recorded with a photographic camera. There are known systems for displaying the images in different formats on the CRT screen and for recording the images correspondingly on photographic film. For instance, a CRT may be controlled so that the image occupies the whole area on the screen, in which case the whole area of the film will be covered in one exposure or the same or another CRT may be controlled with a formatter to display a sequence of smaller images for being recorded on adjacent film areas. A formatter is described in U.S. Pat. No. 4,075,485 which is owned by the assignee of the present invention and is incorporated herein by reference.

In evaluating cardiac function with an ultrasonic camera system or a gamma camera system, it is necessary to make repeated exposures of the heart while the heart is in the same state during each cycle. Most commonly, the QRS complex or R-wave of the electrocardiogram (ECG) waveform is used as a reference point for initiating each exposure because the R-wave is a strong signal. It is conceivble that one of the lower amplitude portions of the ECG waveform such as the P-wave or T-wave could be used as the reference under proper circumstances. Moreover, oscillatory signals such as are obtained with ultrasonographics equipment corresponding with regularly occurring physiological events such as heart beats could be used as a reference. There are known systems for gating the gamma camera output or for turning on the CRT display only during short window intervals in each cardiac cycle. This is achieved with a delay control which varies the time between the R-wave occurrence and the window opening time when recording of a particular exposure is initiated. The CRT recorder is, in effect, turned on and off for one or more brief window intervals during each heart cycle and only radiation integrated during those intervals contributes to forming the image or sequence of images. Information lying outside of any exposure interval is rejected. This produces the stop-motion effect.

A typical gamma camera diagnostic procedure is to determine the left ventricular ejection fraction (LVEF) of the heart which is a measure of the ability of the left ventricle (LV) to eject blood. It is calculated from the following formula:

$$LVEF = EDV - ESV/EDV$$

EDV is the left ventricular end-diastolic volume and ESV is the left ventricular end-systolic volume of the heart. The normal value for LVEF is 59%±6%. At EDV, the heart is filled with blood and has maximum volume. At ESV, the left ventricle has contracted, much of its blood has been expelled and its volume is minimum. If the heart is infused with blood containing a radioisotope, usually technetium99m (Tc99m), it will emit radiation or gamma rays in a pattern which defines the entire range of heart sizes and shapes between diastole and systole. Hence, to get its shape or the blood volume it contains at the end of systole or the end of diastole it is necessary to stop motion and make exposures at these times. There is not enough radiation to make a readable image during one exposure interval so exposures at the same time in successive heart cycles have to be made. As implied above, the present state of the art permits making short systole and diastole exposures after fixed delays following occurrence of an R-wave. However, patients undergoing examinations of this type usually have some cardiac malfunction. As a result, the heart does not beat as rhythmically as it would in a normal healthy person but there are premature ventricular contractions which upset the rhythm. These PVCs cause false triggering of the gamma camera and all of the exposures are not made at a corresponding time within each heart cycle.

SUMMARY OF THE INVENTION

In order to facilitate non-invasive, cardionuclear imaging such as equilibrium, gated blood pool and ejection fraction studies, the gamma camera system must have a device that is capable of processing physiological signals for controlling a variety of camera system functions.

In accordance with the invention a synchronizer, also called an extrasystole rejector, is provided for rejecting the arrhythmic heart beats in order to prevent erroneous data from being added to the gated images during a study which typically encompasses hundreds of cardiac cycles. Of the many types of arrhythmias produced by the heart, the new synchronizer rejects the most common types which are single, or infrequent beat, extrasystoles. Extrasystoles are simply premature contractions of the heart which may be either ventricular, atrial or nodal in origin. The new synchronizer receives patient electrocardiogram signals and gates gamma camera data tallying, data presentation and data recording at preselected periods within the cardiac cycle. The gating intervals, or windows, occur after operator selected delays from the R-wave or other reference point in the ECG or other physiological waveforms and reoccur at the same points in time for each cardiac cycle.

The new arrhythmia rejection circuit (1) rejects the PVC itself; (2) rejects the beat immediately following the PVC, if the heart does not pause to compensate for the PVC and reestablish rhythm, but if a compensatory pause occurs, the following beat is accepted as normal; and (3) disables all gating window circuit functions when the PVC occurs and they remain disabled until a beat in normal rhythm is recognized.

In general terms, the illustrative embodiment of the new synchronizer and arrhythmia rejection circuit employs an electrocardiogram to obtain the usual ECG waveform. Means are provided to produce a flag pulse for every QRS complex or R-wave in the ECG waveform. In one circuit, these R-wave or QRS flag pulses of constant duration and amplitude are integrated to produce an analog voltage signal which is proportional to flag pulse rate and, hence, to heart rate. An essentially conventional rate meter circuit may be used.

The QRS flag pulses are also supplied to the arrhythmia rejection circuit. It has an integrator which is turned on and produces an output ramp voltage that is supplied to a comparator which compares this voltage with a reference voltage. The reference voltage is set to correspond with a certain percentage of the time between QRS flags that correspond with normal heart rate or rhythm. When the ramp voltage equals the reference voltage the comparator trips or changes state. Any premature QRS flags occurring during integration are locked out. This is done by controlling a gating device such as a one-shot multivibrator to which all QRS flag pulses are supplied and which supplies output pulses only if it is enabled and not locked out as a result of the comparator not having changed its state. Thus, the one-shot multivibrator produces output pulses only if the QRS flag pulses are sufficiently spaced to approximate the spacing between QRS flags or R-waves occurring at the normal heart rate. The pulses from the one-shot multivibrator are used to initiate image integration at the proper times as mentioned previously.

In the illustrative embodiment, R-waves which are detected in the ECG waveform and which are determined to be in synchronism with normal or regular sinus rhythm are used as reference points for gating image forming data to the display or recording devices but it will be understood that other parts of the ECG waveform such as the P-wave or T-wave could also be used. Moreover, the reference signals do not necessarily have to be based on the examination subject's ECG. Any signal indicative of physiological activity such as signals of heart activity obtained with cardiosonographic apparatus may be employed and the new rejector will distinguish physiological events which occur at a substantially regular rate from those events that do not.

The basic object of this invention is to provide means for eliminating or rejecting arrhythmic physiological signals in real time so an image recording device will be enabled or gated only in response to heart beats occurring in normal heart rhythm. An adjunct to this object is to reject any signals derived from heart activity immediately following a PVC if the heart does not pause to compensate for the PVC and reestablish normal rhythm.

How the foregoing and other more specific objects are achieved will be evident in the more detailed description of a preferred embodiment of the invention which will now be set forth in reference to the drawings.

DESCRIPTION OF THE DRAWINGS

FIG. 2 is a diagram of one type of image format that can be obtained on the screen of a cathode ray oscilloscope display which is used in FIG. 1;

FIG. 3 consisting of parts A–F shows ECG waveform timing diagrams which are useful to explain the invention;

FIG. 4 is another ECG waveform which is useful for explaining the invention.

DESCRIPTION OF A PREFERRED EMBODIMENT

Figure 1:
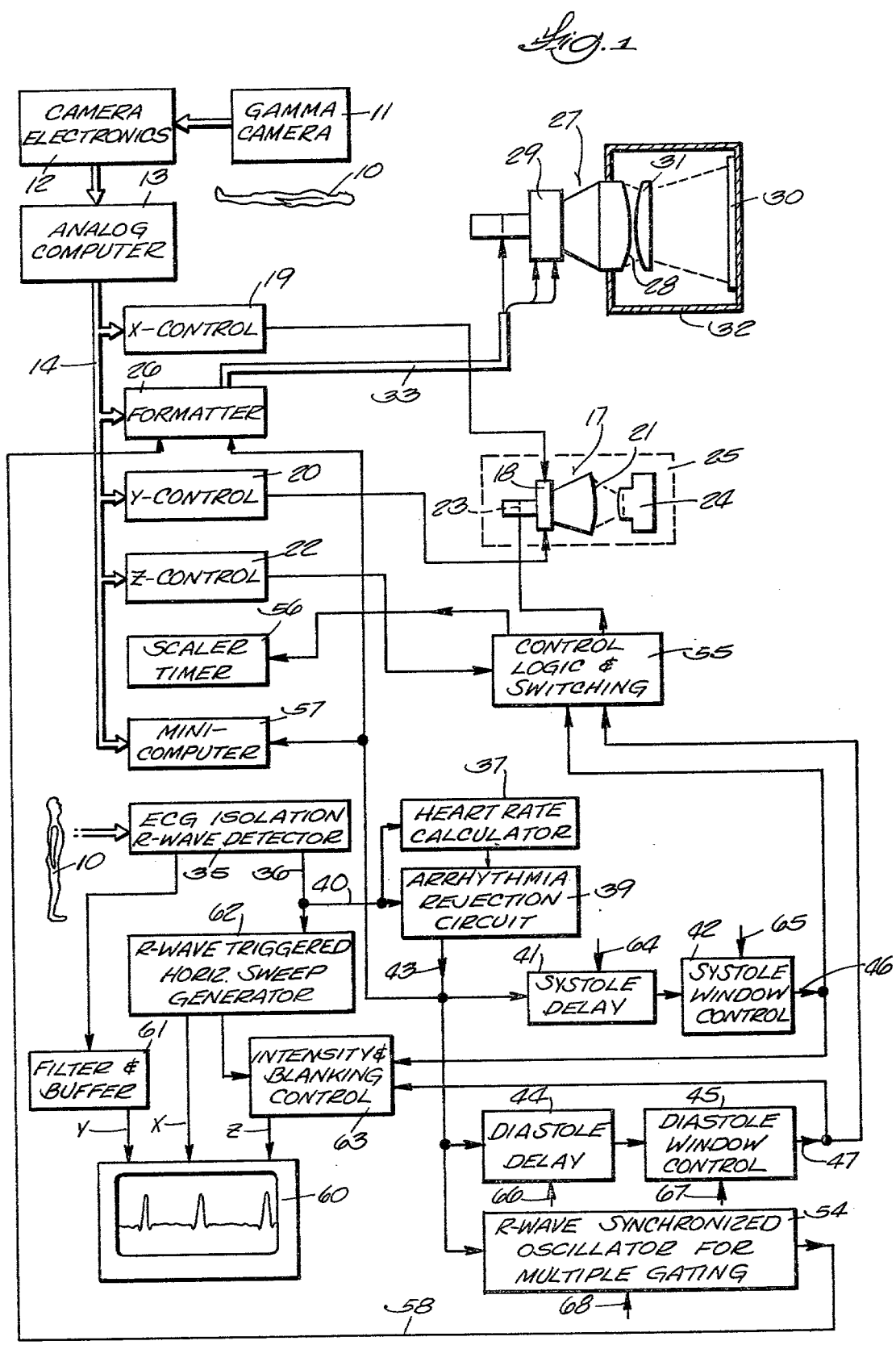
FIG. 1 is a block diagram of a gamma camera system and the new arrhythmia detection and rejection system.

Referring to FIG. 1, a heart patient is represented by the pictograph marked 10. For the purposes of discussion, it may be assumed that the beating heart of this patient and the blood which it pumps are infused with a radioisotope which emits gamma radiation. One of the medical procedures which may be accomplished is to determine the blood volume in the left ventricle of the heart at the end of diastole when it contains maximum blood volume and also at the end of systole when it contains minimum blood volume. The object might be to determine the left ventricle ejection fraction (LVEF) for evaluating the pumping efficiency of the heart as mentioned earlier.

To perform this procedure, a conventional gamma camera 11 such as an Anger type camera, is disposed over the body 10. Although the details are not shown, it will be understood that gamma camera 11 has a crystalline disk which produces scintillations in response to absorption of gamma ray photons radiated from the isotope in the infused heart. An array of photomultiplier tubes in the camera, intercepts the scintillations and produces output signals which are fed to camera electronics module 12. This module, in which the signals are processed, cooperates with an analog computer 13 that computes the x and y coordinates of the scintillations. Signals representative of the energies of the scintillations are supplied to a pulse height selector, in the camera electronics, not shown, and signals falling within the window of the selector are caused to produce z signals which are outputted on cable 14. Valid x and y coordinate representative signals are also outputted on cable 14. The z signals are effective to unblank a cathode ray tube (CRT) 17 in correspondence with the electron beam of the tube being deflected to the point defined by the x and y coordinate signals which are processed in the camera electronics and are delivered to the horizontal and vertical deflection coils 18 of the CRT 17. When the CRT is unblanked, a light spot, corresponding positionally with a scintillation, appears on its display screen 21. The x coordinate signals are supplied to deflection coils 18 through a suitable control 19 which processes the signals to effectuate proper deflection of the CRT beam in the x direction. Circuitry for controlling deflection in the y direction is symbolized by the block 20. Circuitry for controlling z signals which unblank the cathode ray tube beam to produce a light spot on the screen 21 of CRT 17 for every pair of x and y coordinate signals simultaneously produced is represented by the block marked 22. The z signals are supplied to a control logic and switching circuit which gates them at appropriate times to the control grid 23 of the CRT 17 as will be discussed in more detail later. Z signals would normally be supplied directly to the control grid 23 in the absence of the new synchronizer.

Thus, in a conventional manner, light spots corresponding with scintillations corresponding with particular points in the patient's heart are repeatedly developed on screen 21 of CRT 17. If the process is permitted to persist long enough, scintillations from all points on the heart will be gathered and the shape of the heart and its chambers will be defined. Of course, if a continuous exposure is made while the heart is expanding and contracting as it fills with blood and discharges blood, the image will be blurred since the points from which gamma photons are emitted would be continuously in motion or spread out over the area of the heart. The new synchronizer enables exposures to be made during the same short gate intervals in a succession of heart cycles to obtain the equivalent of stopping motion. A unique feature of the new synchronizer is that it inhibits gating of signals for recording if they are related to certain irregular physiological events such as to an R-wave that corresponds with an extrasystole or PVC.

In FIG. 1, the light spots which appear on the screen 21 of CRT 17 are integrated on a film in a camera 24 which is in a light-tight enclosure 25. The film integrates the light spots during each exposure and forms the image of the heart and its blood-filled chambers.

Another CRT 27 is provided to enable displaying a formatted sequence of images on its screen 28. The images are integrated on a film 30 by projecting them with a lens in a light-tight enclosure 32. These successive images would be the result of making a sequence of exposures at differently phased short intervals in successive heart cycles. An image formatter system is provided and is symbolized by the block 26 in FIG. 1. A suitable formatter is described in U.S. Pat. No. 4,075,485 which is owned by the assignee of this application and is incorporated herein by reference. The formatter, in effect, applies a fixed bias to the x and y deflection coils 29 of CRT 27 so that the image or images are formed on screen 28 at a determinable location and within bound areas. The x, y and z signals are supplied to the CRT by way of respective lines collectively designated by reference numeral 33.

A typical format is shown in FIG. 2 where there could be as many as 42 small images formed by recording light-dot after light-dot on screen 28. The light dots are projected to the film in cassette 30 where they are integrated successively. The images on the screen are indicated as small circles. In this particular example, there are six-by-seven images giving a total of 42. It should be understood, however, that if the normal heart rate is fast, there may be time for fewer than 42 individual images to be formed on one sheet of film in cassette 30. For instance, in a practical embodiment the format control is such that five milliseconds must elapse between consecutive views or exposures and adding that time to the time required for each exposure sets the limit for the number of exposures that can be obtained between normally and regularly spaced R-waves.

The formatter 26 permits integrating light spots for a sequence of views at different sequential points of the heart cycle between substantially equally timed physiological reference signals such as R-waves occurring at the regular normal heart rhythm. The end result is an orderly sequence of views of the heart at different stages from diastole-to-systole-to-diastole, etc. A regularly occurring R-wave starts the first view, then after five milliseconds the formatter shifts the image on the display screen 28 and the second view is made. This is repeated for five or ten minutes, usually, to form good images of the ventricle or blood volume shape at many different times in the heart cycle.

As indicated, the exposure time itself is variable. The patient's heart rate determines how many of the 42 separate views obtainable in this case will be filled up. If, let us say, only 17 views, as indicated by the solid line circles in FIG. 2, could be taken before another regular or normal rate R-wave occurred, the formatter would reset so it would go back to No. 1 view again to start building it up. To assure getting as many as 42 separate views between regular heart beats, the operator may shorten the exposure time for each view so more steps may occur before the next valid R-wave, and not an extrasystole, caused a reset.

If PVCs occur at any time during the sequence of heart cycles, they could trigger the gamma camera and formatter to gate images which are out of phase with others in the sequence on the display screen which would cause those images following a PVC to be blurred. The new synchronizer uses only substantially fixed rate physiological signals such as R-waves that occur in substantially the normal rhythm of the heart for all system timing and rejects false-triggering R-waves resulting from PVCs.

As in FIG. 1, another component usually found in gamma camera systems for making heart studies is a scaler timer which is symbolized by the block marked 56. The scaler timer is gated by the z signals produced by the new synchronizer or rejector 39 to count scintillation events at predetermined times. Control logic and switching circuit 55 determines when scaler timer 56 is to start counting for a short interval or during a window interval. The windows are determined by action of the systole delay 41, systole window control 42, diastole delay 44 and diastole window control 45 as will be discussed further. One example might be counting for selected short intervals at diastole when the left ventricle is filled and at systole when the left ventricle blood volume is at a minimum. The number of scintillation counts at diastole and systole are, therefore, indicative of left ventricle volume if that is the nature of the study being made. To find LVEF, for example, the equation given earlier can be used where the number of counts at the end of diastole would be substituted for EDV and the number of counts at the end of systole would be substituted for ESV. Of course, counting by the scaler timer must be initiated only by valid physiological signals such as R-waves or QRS flags which fall within the natural rhythm of the heart and not by signals that correspond with PVCs.

Known gamma camera systems for heart studies also usually include a minicomputer which is symbolized by the block 57. The minicomputer is programmed for using scintillation events to produce a number of indications of heart function. It can also be used for calculating LVEF, for example. It must be provided with information as to when valid R-waves or other regularly occurring reference signals have occurred, that is, R-waves which fall within the natural rhythm of the heart and are not extrasystoles. Hence, the new synchronizer can provide the minicomputer, for example, with valid R-wave flag signals which are indicative of certain events being of significance in a long chain of continuous scintillation data so the minicomputer can make all of its calculations with the use of valid physiological reference points which are the R-waves, in this example, that are associated with normal heart beating rate with the exclusion of PVCs.

In FIG. 1, all timing is based on detection of valid normal rhythm QRS complexes or R-waves occurring in the ECG. Detection is accomplished with an ECG isolation and R-wave detection circuit which is symbolized by the block 35 in FIG. 1 and is basically known. It couples to the same patient 10 that is in view of the gamma camera at the time. Its output on line 36 is a series of square wave pulses, called flag pulses, which coincide in time with R-waves or QRS complexes that are incidental to normal rhythmic heart beats and also to premature ventricular contractions or extrasystoles.

Pulses that correspond with R-wave flag pulses which occur at a rate corresponding with the normal and substantially regular heart rate are called clock pulses herein. The clock pulses are used for initiating counting or recording scintillations which represent various stages of heart activity.

One use of these QRS flag pulse signals is in a heart rate calculator which is symbolized by the block 37 in FIG. 1. The heart rate calculator integrates the incoming pulses, which are mostly normal rhythm pulses, and produces an analog voltage signal whose magnitude corresponds with the repetition rate of QRS complexes or, in effect, the heart rate. This signal is supplied by way of a line 38 to the new arrhythmia rejection device or circuit which is represented by the block 39 in FIG. 1. The QRS flag pulses from R-wave detector 35 are also supplied to arrhythmia rejection circuit 39 by way of a line 40. The manner in which the analog voltage signal indicative of heart rate and the R-wave flag signals are utilized in the arrhythmia rejection circuit 39 will be explained in greater detail when the latter is described in reference to FIG. 5.

FIG. 3, consisting of parts A-F, illustrates an electrocardiogram waveform in part A which will serve as a basis for discussion. This ECG has a series of QRS complexes and their peaks, known as the R-wave peaks, are marked R1–R8. A ventricular contraction usually occurs coincident with an R-wave. The spacing between R1 and R2, between R3 and R4 and between R6, R7 and R8 in this example are equal and correspond with the normal heart rate which, even in a reasonably healthy heart may vary by about ±10% from one R-to-R interval to the next. A normal heart rate with a subject at rest might be about 72 beats per minute or about 833 milliseconds between beats. An unhealthy heart might beat much faster or much slower. Most patients having a need for heart evaluation will also exhibit premature ventricular contractions or extrasystoles that result from QRS complexes or R-waves falling out of the natural rhythm such as those marked R3 and R5 in FIG. 3 which are indicated by QRS complexes comprised of dashed lines in FIG. 3, part A. The new arrhythmia rejection circuit 39, shown in detail in FIG. 5, would negate or reject PVCs R3 and R5 since they follow valid or normal R-waves R2 and R4 too closely. If R3 were much closer to R4, it might be considered a valid R-wave and not a PVC as will be shown later when the arrhythmia rejection circuit 39 is described in detail.

In FIG. 3, PVC R3 is followed by a long pause before R4 occurs. If the pause is long enough, the new arrhythmia rejection circuit interprets this as restoration of natural rhythm and it follows the mode in which it permits signals for forming an image to be gated to the CRT 17 display to the scaler timer 56 and to the minicomputer 57 at the proper times as dictated by switching circuit 55 as governed by delay and window controls 41, 42, 44 and 45. By way of example, any R-wave that occurs, let us say arbitrarily, within 75% of the interval between successive normal heart rate R-waves might be considered a PVC in which case any occurring within 25% of the time interval preceding the second in a pair of successive R-waves might be considered a valid R-wave and, in accordance with the invention, a clock pulse or timing reference pulse corresponding with a valid R-wave would be produced.

In FIG. 3, part B, under the ECG, there is a time axis line. Some short intervals along this line are marked ED. The duration of these intervals can be set. The ED intervals occur at a time that coincides with the end of diastole when the left ventricle has maximum volume of blood in it. At this point in the heart cycle the diagnostician wants to stop motion and form an image of the ventricle. As will be explained, the short intervals can be adjusted in time relative to accepted or valid R-waves and the length of the intervals can be adjusted using known techniques. It is during these intervals or time windows that the image data is gated to the various image forming and data gathering devices. Also appearing along the time axis is the typical location of short intervals marked ES which coincide with the end of systole or when the left ventricle contains minimum blood volume. Generally, the end of systole occurs at about 40% of the time interval between R-waves such as between R1 and R2 in FIG. 3. Thus, the lengths of both intervals ED and ES must be settable relative to successive R-waves and the lengths of the intervals must be variable. This is accomplished in FIG. 1 with some conventional circuits which are symbolized by blocks 41 and 42 for the systole delay and systole window intervals. The circuitry in the systole delay block 41 sets the location of ES interval relative to the preceding R-waves such as R1 in FIG. 3. The systole delay may be anything from 0 to 1500 ms. The circuitry in the systole window duration controller 42 is adjustable to set the duration of the interval ES. The ES intervals in an actual embodiment are adjustable between 0 and 300 ms. The systole delay and window circuits, 41 and 42, are clocked only in correspondence with valid R-wave flag pulses occurring at what is considered the normal rhythm of the heart and which come out of arrhythmia rejection circuit 39 on line 43.

In FIG. 1 there is also a block 44 representative of the circuitry for the diastole delay which locates the interval ED in FIG. 3 relative to successive clock pulses corresponding with valid R-waves. There is also a block 45 containing the circuitry for controlling the duration of the ED or end diastole window of FIG. 3. The outputs from the systole and diastole delay devices and the systole and diastole window duration setting devices are sent, by means of lines 46 and 47, in FIG. 1 to various devices that require gated signals. Signals representing the systole and diastole delay and open gate or open window durations are also sent to the control logic and switching circuit 55 which outputs the gating signals at appropriate times for turning the scaler timer 56 and CRT 17 on and off as required. Clock pulses corresponding with valid R-waves coming out of arrhythmia rejection circuit 39 on line 43 are also fed to a block bearing the legend R-wave synchronized oscillator 54 which is used for multiple gating such as is accomplished with formatter 26. Block 54 responds to clock pulses corresponding with valid R-waves by providing signals which are sent over line 58 to the formatter circuit 26 that controls stepping of the images along the display screen 28 of the CRT 27 to enable obtaining as many views of the heart in variously blood-filled states as are desired. The formatter also receives the clock pulses outputted on line 43 from arrhythmia rejection circuit 39 so the formatter will only start each image in a sequence of images displayed on CRT screen 28 if there is synchronism with or reference to a clock pulse.

Referring further to FIG. 1, the physiological waveform on which synchronism of the system with regularly occurring physiological events is based is displayed on a cathode ray tube monitor 60. The particular physiological event used and displayed in this example is the ECG waveform. The ECG waveform signals from ECG detector 35 are fed through a filter-buffer device, symbolized by the block 61, which provides the y axis deflection signal to monitor 60. The synchronizer has associated with it an R-wave triggered horizontal sweep generator which is symbolized by the block 62. The sweep generator responds to detected R-waves by initiating x-direction deflection of the waveform on the monitor screen. The monitor brightness or intensity and blanking control is represented by the block 63. The CRT is of the persistence or slow decay type. Successive ECG waveforms appear on it and persist until replaced by ensuing waves. The intensity and blanking control 63 responds to the signals coming from delay signal output lines 46 and 47 and indicative of the delays and windows associated with the gating intervals such as ED and ES in FIG. 3 by modulating the ECG waveforms to high brightness during these intervals. This is exemplified in FIG. 4 where the bright ED and ES gating intervals are correspondingly marked as they appear superimposed on the ECG waveform.

The specified example of the new arrhythmia rejection circuit, which is shown at block 39 in FIG. 1, will now be described in reference to the FIG. 5 circuit diagram.

Figure 5:
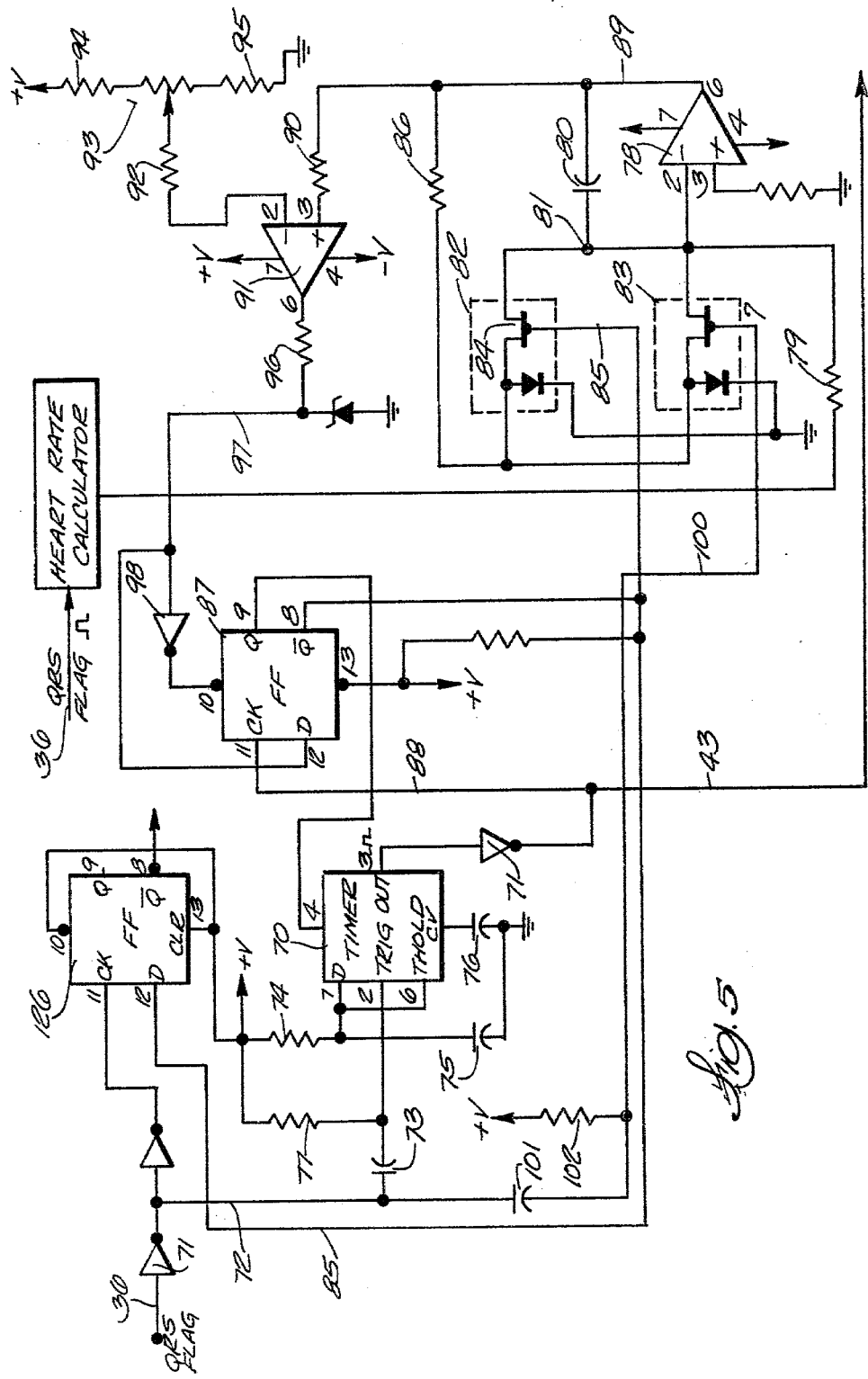
FIG. 5 is a detailed schematic diagram of the arrhythmia rejection circuit.

In FIG. 5 there are two inputs for the continuous sequence of R-wave or QRS signals that are delivered from the ECG isolation and R-wave detection block 35 and are outputted on line 36 in FIG. 1. This line 36 is correspondingly marked in FIG. 5 as line 36 to heart rate calculator 37 and as line 36 constituting the QRS flag signals to the depicted arrhythmia rejection circuit. There is a QRS flag pulse input for every ECG QRS complex which occurs whether it is one at the natural heart rhythm rate or a PVC. The QRS flag pulses are shown to be in coincidence with R-waves R1-R8 in part C of FIG. 3 where exemplary flag pulses are marked 103-106.

The output line for clock pulses which correspond with valid R-wave or QRS flag pulses that occur at the normal heart rate and are usable for synchronous clocking of the minicomputer 32, formatter 26, the systole and diastole delay and window controls 41, 42 and 44, 45 and the multiple gating oscillator 54 are outputted from the FIG. 5 circuit on line 43. These clock pulses corresponding with R-wave pulses occurring at a regular rate are outputted from pin 3 of a one-shot multivibrator (MV) 70 through an inverter 71. MV70 serves as a clock pulse gate which is enabled and disabled in accordance with whether the physiological events being detected are in or out of rhythm. By way of example and not limitation in an actual embodiment, an NE555 timer was used for the one-shot MV70. Also by way of example, the output clock pulses from pin 3 can typically have one millisecond durations and be at TTL voltage levels. MV70 serves as an R-wave clock for the utilization circuits which were described above. In this design, MV70 acts like a switch which gates incoming QRS flag pulses to its output pin 3 when properly timed R-waves in a sequence of R-waves have been detected, that is, only R-waves which are in synchronism with the normal rhythm or R-wave rate of the heart.

The positive going QRS flag pulses are fed in from line 36 through an inverter 71, a line 72, a differentiator capacitor 73 and resistor 77 and to trigger signal input pin 2 of one-shot MV70. The one-shot MV has the usual RC timing circuit consisting of resistor 74 and capacitor 75, and a noise filtering capacitor 76.

In the lower right area of FIG. 5 there is an operational amplifier (op-amp) 78 connected as an integrator and having a fixed input resistor 79 and an integrating capacitor 80. One side of capacitor 80 and resistor 79 connect to a common point 81 which also connects to the inverting input pin 2 of op-amp 78. The input to pin 2 is the variable analog voltage signal corresponding with the integrated or substantially average of regular or normal heart rate provided by the heart rate calculator 37 over line 38. The DC voltage level at point 81 and pin 2, therefore, is proportional to the patient's heart rate in beats per minute. There are two analog switch elements 82 and 83 connected in the input circuit of op-amp 78. Analog switch 82 has a field effect transistor 84 with a line 85 being connected to its gate terminal. When analog switch 82 is made conductive by an appropriate signal being applied to the gate of transistor 84, integrating capacitor 80 is short-circuited and therefore discharged through a resistor 86 and transistor 84 so amplifier 78 cannot integrate. The output pin of op-amp 78 is pin 6.

Analog switch control line 85 is the output line from the $\overline{Q}$ output pin 8 of flip-flop (FF) 87. The clock pulses from the output pin of one-shot MV70 are fed by way of line 88 to the clock input pin 11 of FF87. The rising edge of each clock pulse causes pin 8 or the $\overline{Q}$ pin of FF87 to go high which turns off the channel inside of analog switch 82. This removes the short circuit across integrating capacitor 80 which is then allowed to charge and integrate through resistor 86. This results in a positive-going ramp output from pin 6 of op-amp integrator 78. The ramp signal is coupled by way of line 89 and an input resistor 90 to the non-inverting input pin 3 of an operational amplifier 91 which is connected as a comparator. The non-inverting input pin 2 of comparator 91 is connected through a resistor 92 to a potentiometer 93. The potentiometer is connected in a series circuit with resistors 94 and 95 and the series circuit is connected between DC supply and ground. Potentiometer 93 is characterized as the extrasystole inhibit potentiometer. The reference voltage level at which potentiometer 93 is set determines the time range within which QRS complexes in the ECG waveform are to be considered PVCs or extrasystoles.

Thus, the positive-going ramp from integrator op-amp 78 is repeatedly compared by comparator 91 with the extrasystole inhibit or reference signal derived from potentiometer 93. When the voltage ramp on non-inverting input pin 3 of comparator 91 reaches the reference voltage level on the inverting input pin 2, the comparator 91 trips and its output pin 6 goes high. The high going signal is coupled through a resistor 96, a line 97 and an inverter 98 to the reset pin 10 of FF87. This changes the state of pin 8 of FF87 which thereby operates analog switch 82 so it resets the integrator by discharging capacitor 80. The conditions at pin 10 and 12 of FF87 are now such that integration will begin when the next clock pulse from one-shot MV70 comes along. Note that the output Q pin 9 of FF87 goes low during integration and output $\overline{Q}$ pin 8 goes high to start integration.

The ramp output of integrator op-amp 78 is reset to ground when either of the channels in analog switches 82 or 83 become conductive. Analog switch 83, it will be noted, is connected in parallel with analog switch 82 so both have the ability to discharge integrator capacitor 80. The channel in analog switch 82 is closed each time a normal QRS complex and corresponding clock pulse occurs, because for every such event pin 8 of FF87 is clocked to go high by a clock pulse from one-shot MV70. Thus, pin 8 of FF87 goes high to start integration and stays high until a comparison is made and a reset signal is received on pin 10 of FF87 through inverter 98 from output pin 6 of comparator 91. On the other hand, the other analog switch 83 closes its channel in response to QRS flag signals whether they correspond with normal or premature heart beats. This is so because control gate pin 7 of analog switch 83 connects by way of line 100, in which there is a coupling capacitor 101, to line 72 which feeds in both normal and premature QRS flag pulses.

All QRS flag pulses corresponding with heart beats, whether premature or not, are inputted to trigger pin 2 of one-shot MV70 for triggering it. If they are at the normal heart rate, a one millisecond output pulse appears on pin 3 of multivibrator 70 as mentioned earlier. If they are PVCs, output pin 3 is inhibited and no system clock or valid rhythmic R-wave indicating clock pulse is delivered to the various utilizing devices over line 43.

An example of the manner in which the arrhythmia rejection circuit of FIG. 5 functions will now be given and reference will also be made to the timing diagrams in FIG. 3. Assume that the first R-wave or QRS complex detected is in the normal rhythm and is the one marked R1 in FIG. 3. In such case, a one millisecond pulse, such as 107 in part D of FIG. 3, from pin 3 of one-shot MV70 is fed to the clock input pin 11 of FF87. The flip-flop 87 will change the state on its $\overline{Q}$ pin 8 which goes high to start integration by capacitor 80. The high state turns off short-circuiting transistor 84 in analog switch 82 to start integration. During integration, the ramp output of op-amp 78 is compared to the extrasystole inhibit reference voltage level from potentiometer 93. When the comparator 91 trips and its output pin 6 goes high, the signal is coupled to the reset input pin 10 of FF87, causing its $\overline{Q}$ output pin 8 to go low again. The trip level of comparator 91 is indicated in part E of FIG. 3 which shows successive ramp signals. Pin 8 of FF87 going low constitutes a reset command to analog switch 82 which means that the switch is short-circuiting capacitor 80 again and preventing integration.

The Q output or pin 9 of FF87 is low while integration is taking place and high while the reset condition exists. This output pin 9 controls the clear or reset input pin 4 of the one-shot clock MV70. When the clear pin 4 is low, the one-shot MV cannot output a one millisecond pulse on line 43 which means that the utilization devices are not clocked while the one-shot multivibrator 70 is inhibited or in a clear state. It will be apparent then that if the reference voltage level set by the extrasystole inhibit potentiometer 93 resulted in a pulse width on the clear pin 4 of one-shot MV70 that was a percentage of the total time between normal heart beats, then a lockout period between R-waves is established. During this period, any premature beat that occurs is ignored. A typical normal lockout or inhibit interval is designated in part F of FIG. 3.

FIG. 3 shows two successive QRS flag pulses 103 and 103 which are coincident with normally spaced QRS complexes R1 and R2. For each of these there is a one millisecond clock pulse 107 and 108 produced by one-shot multivibrator 70 and supplied to the utilization devices over line 43. The ramp voltage from op-amp 78 for these two normal QRS complexes is marked 109. The lockout period during which one-shot multivibrator is inhibited or disabled from producing any one millisecond clock pulses is marked 110 and is coextensive in time with ramp 109. The lockout period is represented by the state or voltage on pin 9 of FF87. The lockout period is governed by the extrasystole inhibit reference voltage setting and is typically set for 75% of the normal rhythm R-wave-to-R-wave interval.

The example of a PVC occurring corresponding with the QRS complex R3, shown in dashed lines, between normal rhythm beats R2 and R4 is also depicted in part A of FIG. 3. It will have a corresponding QRS flag pulse 104 but since the output of one-shot MV70 is still inhibited because the ramp 109' in part E has not reached trip level, it will not produce a one millisecond clock pulse at the time where such pulse might have otherwise occurred as is depicted in dashed lines and marked 111 in FIG. 6. However, the QRS flag pulse due to the PVC marked R3 will trigger the gate of analog switch 83 and make it conductive momentarily to discharge capacitor 80 and thereby restart the integration period as indicated by the second ramp 112 in FIG. 6. The lockout period, that is, the period during which pin 10 of FF87 will not get a reset signal from comparator 91, will be extended as indicated by its waveform 113 in part F of FIG. 3. Analog switch 83, it should be noted, is made conductive by QRS flag pulses associated with normal rate and PVC R-waves. The flag pulses are fed from input line 72 through a differentiator capacitor 101 and resistor 102. An incoming QRS flag pulse pulls the gate pin 7 of analog switch 83 down to make the switch conduct.

FIG. 3 shows how a QRS complex R6 is also rejected if, in the example, it is in close proximity in time to a PVC marked R5. As indicated, any PVC causes a reset signal to be sent to analog switch 83 to make it conductive for discharging and resetting integrating capacitor 84. It is evident in part E of FIG. 3 that integration is in progress at the time of the PVC marked R5 but the trip point of the comparator 91 has not been reached at this time as indicated by the shorter than normal ramp 114. Because of the QRS flag pulse triggering the capacitor discharging analog switch 83 to conduct, integration restarts and a new ramp starts at point 115. The new ramp extends the lockout period. The momentary reset was not ordered by the control flip-flop 87 because it cannot change state until the comparator 91 trip point is reached. The next QRS complex R6 will also extend the lockout period unless it occurs so long after the PVC at R5 as to correspond with normal heart rhythm. For example, assume that a normal QRS complex R6 occurred as indicated while the one-shot MV70 is inhibited or locked out so that the R-wave clock pulse 117', in dashed lines in part D of FIG. 3, did not occur. Of course, the QRS flag 105 would have occurred and would have reset the integrator by reason of the QRS flag pulse being applied to analog switch 83. Then, in FIG. 3, a new ramp 118 would be started and if sufficient time elapsed for the comparator 91 to reach the trip point, the lockout period 119 would be extended until the trip point was reached in which case FF87 would change the states of its outputs and one-shot MV70 would become inhibited. Then, since the next ensuing QRS complex R7 would lie outside of the lockout period 119, its occurrence would result in a one millisecond synchronizing clock pulse being emitted by one-shot MV70 to output line 43 in FIG. 5. Clock pulses in correspondence with normal rhythm would then be restored. Thus, if the heart does not pause naturally long enough to compensate for the PVC marked R5 and reestablish rhythm at R6, the R6 QRS complex and heart beat following the PVC marked R5 is rejected, that is, no clock pulse is produced. If the heart does pause, the ramp voltage will have time to reach a point where it will cause the comparator 91 to trip and this corresponds with substantially normal rhythm having been attained as is the case where R7 occurs.

It will be evident that all gating window circuit functions are disabled when a PVC occurs and that they will remain disabled until a beat in normal rhythm is recognized.

Another kind of rejection is obtainable with the circuitry in FIG. 5 and involves a D type flip-flop marked 126. All normally spaced and premature detected QRS complexes or QRS flag pulses are allowed to clock this flip-flop on its clock pin 11. The integrate and reset command pulses from FF87 are fed into pin 12 of flip-flop 126. When a PVC occurs during a lockout period and pin 12 of flip-flop 126 is high as is pin 8 of FF87, the output on the $\overline{Q}$ pin 8 of flip-flop 126 will change state or go low. It will stay low until the next normal rate QRS complex and heart beat occurs and then go high. If another PVC occurred, it would not go high because the lockout period is still in effect. The pin 8 output of flip-flop 126 is tied to the clear lines 65, 67 and 68 in FIG. 1, which are the clear lines for one-shot multivibrators, not shown, in the systole, diastole and multiple gating circuits 42, 45 and 54. Upon occurrence of a PVC, these clear lines are pulled low to disable these circuits. They remain disabled until a normal beat has been recognized.

In summary, the invention may be broadly characterized as a device for detecting in a sequence of physiological signals, which are mostly occurring at a substantially uniform rate or in a regular rhythm, those signals which occur arrhythmically. The device produces synchronizing clock pulses coincident with signals that are determined to be rhythmic. The clock pulses may be used for synchronizing a variety of medical electronic devices.

I claim:

1. A gamma camera system including a gamma camera and means for producing signals corresponding with the x and y coordinates of radiation events corresponding with radiation emitted from a plurality of points in a beating heart and for producing z signals coincident with predetermined x and y coordinate signals, image display means including a cathode ray tube controlled by said coordinate signals to display radiation events at corresponding coordinates on the screen of said tube and including means for unblanking said tube in response to occurrence of z signals to effect display of each event as a light spot on said screen to thereby form images of the heart by integration of said light spots, a device for distinguishing in a sequence of heart activity indicating signals those signals which are associated with heart beats occurring at regular nominally normal intervals from those signals which occur within a predetermined percentage of the time before expiration of said intervals, gate means having input means for receiving all signals indicative of heart beats, said gate means being operative to produce a clock pulse coincident with a received signal when said gate means is enabled, means responsive to occurrence of said signals by initiating measurements of time periods, means responsive to a measured time period exceeding a predetermined percentage of a regular time interval by enabling said gate means to produce a clock pulse coincident with the next heart activity indicating signal that is received by said gate means, diastole delay control means responsive to occurrence of said clock pulses by determining first repeatable delay intervals during heart cycles which follow clock pulses and diastole window control means for establishing short second intervals designated as window intervals, systole delay control means responsive to occurrence of said clock pulses by determining third repeatable delay intervals during heart cycles which follow clock pulses and systole window control means for establishing short fourth intervals designated as window intervals, and means responsive to occurrence of said second and fourth window intervals by enabling display of radiation events for the duration of said window intervals.

2. The apparatus as in claim 1 including:

scaler-timer means for counting radiation events and responsive to occurrence of said windows by counting events for the durations of the respective window intervals.

3. The apparatus as in claim 1 including:

second display means including a cathode ray tube having a screen and formatter means for controlling said second display means to form images on adjacent areas of its screen to thereby enable the heart to be imaged at different stages of expansion and contraction, said formatter means being operative to effect shifting from one image area to the next in response to occurrence of clock pulses.

4. The device as in claim 1 wherein:

said means for measuring time periods comprises integrator means including an operational amplifier having input and output means and an integrating capacitor connected between said input and output means, means for supplying to said input means a first analog signal corresponding in magnitude with normal heart rate, said operational amplifier responding to input of said analog signal by producing a ramp signal on its output means, first and second selectively nonconductive and conductive electronic switches, respectively connected for discharging said capacitor when made conductive to thereby reset initiation of the measurement of said time periods, means for providing a second analog signal representative of a percentage of the time between regular heart beats, comparator means for comparing said ramp signal with said second analog signal and operative to trip in response to said ramp signal exceeding said second analog signal, a flip-flop responsive to said comparator means being untripped by staying in a lockout state wherein it cannot change state, said flip-flop being connected for being clocked by clock signals from said gate means and being operative to change state in response to a clock signal when unblocked, said flip-flop having one output terminal coupled to said gate means for disabling and enabling said gate means when said flip-flop is blocked and unblocked respectively, said flip-flop having a second input terminal connected for causing said first electronic switch to be nonconductive when said flip-flop is unblocked to thereby initiate integration and measurement of a time period in response to a clock signal from the output means of said gate means, said second electronic switch means responding to heart activity indicating signals by becoming momentarily conductive to thereby reset said integrator for extending said time period.

5. An arrhythmia rejector for distinguishing R-wave signals in a subject's electrocardiogram (ECG) which are associated with heart beats occurring at a regular normal repetition rate from R-wave signals which are associated with premature ventricular contractions (PVCs) occurring between regular R-wave signals, said rejector being for use in a system which employs successive clock pulse signals corresponding with R-waves as reference points for timed functions in utilization devices, said rejector comprising:

a one-shot multivibrator connected to receive at its trigger signal input means a succession of R-wave signals some of which correspond with normally timed heart beats and others with PVCs, said multivibrator having output means for clock pulses and a reset terminal which when in a first signal state permits a clock pulse corresponding with an R-wave signal at its input means and when in a second state prevents a corresponding clock pulse, integrator means having output means and having input means for first analog signals corresponding in magnitude with occurrence of R-wave signals at normal heart rate and an integrating capacitor connected to said input means, said integrator means being operative to produce on its output means a voltage ramp whose magnitude is a function of the time during which said analog signal is integrated, first and second normally nonconductive switch means each having control gates for control signals corresponding with R-wave signals which cause them to conduct, each of said switch means being connected for discharging said capacitor when they conduct to thereby reset the start of integration time, means for producing a second analog signal whose magnitude is representative of a percentage of the time between R-wave signals corresponding with normal heart rate, a comparator having output means and having input means for said ramp signal from said integrator means and for said second analog signal, said comparator being operative to trip and change the state of its output means in response to said ramp signal exceeding said second analog signal, a flip-flop having a clock pulse and reset terminals and complementary output terminals, said comparator output being coupled to said reset terminal, said clock pulse output from said multivibrator being coupled to said clock pulse terminal, one of said flip-flop output terminals being coupled to said multivibrator reset terminal and the other being coupled to said control gate of said first switch means, means for coupling signals associated with all normal and PVC R-waves to the control gate of said second switch means to restart said integrator for every R-wave, said comparator when untripped controlling said flip-flop to be in a state that results in said second signal state on the reset terminal of said multivibrator to thereby inhibit it from producing a clock pulse before said comparator trips, said comparator when tripped controlling said flip-flop to be in a state that results in said second signal state on the reset terminal of said multivibrator to thereby enable it to produce a clock pulse coincident with an R-wave at its input.

* * * * *

UNITED STATES PATENT AND TRADEMARK OFFICE
CERTIFICATE OF CORRECTION

PATENT NO. : 4,245,647

DATED : January 20, 1981

INVENTOR(S) : Harvey G. Randall

It is certified that error appears in the above—identified patent and that said Letters Patent is hereby corrected as shown below:

Column 15, Line 43, "input" should read --output--

Signed and Sealed this

Fourteenth Day of April 1981

[SEAL]

Attest:

RENE D. TEGTMEYER

Attesting Officer    Acting Commissioner of Patents and Trademarks